United States Patent
O'Shea et al.

(10) Patent No.: US 7,733,233 B2
(45) Date of Patent: Jun. 8, 2010

(54) METHODS AND SYSTEMS FOR MONITORING POSITION AND MOVEMENT OF HUMAN BEINGS

(75) Inventors: Michael D. O'Shea, Neenah, WI (US); Gary A. Clement, Menasha, WI (US); Gary F. Madsen, Greenville, WI (US); John C. Onderko, Appleton, WI (US); Corey B. Mingerink, Appleton, WI (US); Scott J. Buss, Appleton, WI (US); Brian J. Carey, Neenah, WI (US); Jeffrey D. Lindsay, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 283 days.

(21) Appl. No.: 11/552,481

(22) Filed: Oct. 24, 2006

(65) Prior Publication Data

US 2008/0094226 A1 Apr. 24, 2008

(51) Int. Cl.
*G08B 23/00* (2006.01)

(52) U.S. Cl. .............. 340/573.7; 340/573.1; 340/572.1; 340/572.5; 340/575

(58) Field of Classification Search .............. 340/573.7, 340/573.1, 572.1, 572.5, 686.1, 539.11, 575; 600/595; 324/207.11–207.25
See application file for complete search history.

(56) References Cited

U.S. PATENT DOCUMENTS

| | | | | |
|---|---|---|---|---|
| 4,736,196 A | * | 4/1988 | McMahon et al. ....... | 340/573.4 |
| 4,993,245 A | * | 2/1991 | Ott .............................. | 70/57.1 |
| 5,241,300 A | | 8/1993 | Buschmann | |
| 5,515,865 A | * | 5/1996 | Scanlon ...................... | 600/534 |
| 5,570,082 A | * | 10/1996 | Mahgerefteh et al. ....... | 340/604 |
| 5,684,460 A | | 11/1997 | Scanlon | |
| 5,774,055 A | * | 6/1998 | Pomerantz ............... | 340/573.7 |
| 5,825,293 A | * | 10/1998 | Ahmed et al. ............ | 340/573.1 |
| 5,914,660 A | * | 6/1999 | Mesibov et al. .......... | 340/573.7 |
| 6,011,477 A | * | 1/2000 | Teodorescu et al. ...... | 340/573.1 |
| 6,083,756 A | | 7/2000 | Hedner et al. | |

(Continued)

FOREIGN PATENT DOCUMENTS

EP 0 573 765 B1 12/1993

(Continued)

OTHER PUBLICATIONS

PCT International Search Report and Written Opinion dated Mar. 26, 2008 for International Application No. PCT/IB2007/054136.

(Continued)

*Primary Examiner*—Davetta W Goins
*Assistant Examiner*—Hoi C Lau
(74) *Attorney, Agent, or Firm*—Armstrong Teasdale LLP

(57) ABSTRACT

Methods and systems for detecting a predetermined position of a user wearing a disposable absorbent article are given. The methods and systems may include detecting that the user of the disposable absorbent article is in the predetermined position, wherein the predetermined position is determined to be a potentially life-threatening position. In response to determining that the user is in the predetermined position, an operation of a transmitter located on the disposable absorbent article is controlled. Movement, location and/or various biometrics of the user may also be monitored.

22 Claims, 5 Drawing Sheets

U.S. PATENT DOCUMENTS

| | | | |
|---|---|---|---|
| 6,104,295 A * | 8/2000 | Gaisser et al. | 340/573.4 |
| 6,215,403 B1 | 4/2001 | Chan et al. | |
| 6,509,620 B2 | 1/2003 | Hartwell et al. | |
| 6,753,783 B2 * | 6/2004 | Friedman et al. | 340/573.7 |
| 6,769,303 B1 | 8/2004 | Okojie | |
| 6,842,990 B2 | 1/2005 | Taylor | |
| 6,847,892 B2 | 1/2005 | Zhou et al. | |
| 6,968,294 B2 | 11/2005 | Gutta et al. | |
| 6,975,230 B1 | 12/2005 | Brilman | |
| 7,053,781 B1 * | 5/2006 | Haire et al. | 340/604 |
| 7,057,495 B2 * | 6/2006 | Debord et al. | 340/309.16 |
| 7,069,784 B1 | 7/2006 | Eskridge | |
| 7,071,520 B2 | 7/2006 | Reid | |
| 2002/0013538 A1 | 1/2002 | Teller | |
| 2002/0070864 A1 * | 6/2002 | Jeutter et al. | 340/573.1 |
| 2002/0070868 A1 * | 6/2002 | Jeutter et al. | 340/604 |
| 2003/0163287 A1 | 8/2003 | Vock et al. | |
| 2005/0080566 A1 | 4/2005 | Vock et al. | |
| 2006/0066449 A1 | 3/2006 | Johnson | |
| 2006/0174693 A1 * | 8/2006 | Chen et al. | 73/29.01 |
| 2006/0211936 A1 | 9/2006 | Hu et al. | |
| 2006/0214765 A1 * | 9/2006 | Pitchers et al. | 340/3.4 |
| 2008/0110984 A1 * | 5/2008 | Uchitani | 235/385 |

FOREIGN PATENT DOCUMENTS

| | | |
|---|---|---|
| EP | 1 023 871 A1 | 8/2000 |
| GB | 2396043 | 6/2004 |
| WO | WO 99/04691 | 2/1999 |

OTHER PUBLICATIONS

RespiSense Buzz for SIDS, Sep. 20, 2005, available at http://www.medgadget.com/archives/2005/09/respisense_buzz.html.

Cellular Diaper Prevents SIDS, Sep. 22, 2005, available at http://www.gizmodo.com/gadgets/gadgets/cellular-diaper-prevents-sids-126951.php.

Some Babies at Greater Risk for SIDS, Dec. 10, 2004, available at http://72.14.203.104/search?q=cache:QV7T72yYYy0J:www.medicinenet.com/script/main/art.asp%3Fli%3DFOA%26articlekey%3D40999+art.asp%3Farticlekey%3D40999+SIDS+FACEDOWN&hl=en&ct=clnk&cd=1.

New Research Findings Offer Clues For Avoiding Infant Death Syndrome (SIDS), Jan. 3, 2002, available at http://www.talkaboutsleep.com/sleep-disorders/archives/Snoring_apnea_SIDS.htm.

Angelcare® Movement Sensor With Sound Monitor—Two Parent Unit, printed on Oct. 24, 2006, available at http://www.amazon.com/gp/product/B0000E262S/104-1736194-7150303?v=glance.

Sudden Infant Death Syndrome (SIDS), Nov. 30, 2005, available at http://www.emedicinehealth.com/sudden_infant_death_syndrome_sids/article_em.htm.

Microstrain's orientation sensor gets the attention of U.S. Navy, Jul. 8, 2002, available at http://www.smalltimes.com/articles/stm_email_screen.cfm?ARTICLE_ID=267956.

Anwar Sadat et al., "Low-power CMOS Wireless MEMS Motion Sensor for Physiological Activity Monitoring," IEEE Transactions on Circuits and Systems—I: Regular Papers, vol. 52, Issue12, pp. 2539-2551, Dec. 2005.

* cited by examiner

METHODS AND SYSTEMS FOR MONITORING POSITION AND MOVEMENT OF HUMAN BEINGS

BACKGROUND OF THE INVENTION

1. Field of the Invention

Embodiments of the present invention generally relate to human monitoring devices and, more specifically, to detecting when an individual is lying in a predetermined position.

2. Description of the Related Art

Sudden infant death syndrome (SIDS) is a tragic disease in which a young child, with no apparent health issues, may perish suddenly and without warning. SIDS is the leading cause of death of infants between 1 and 12 months old, killing about 2,500 infants in the United States each year. One common cause of SIDS is asphyxiation by blankets and pillows on an infant's bed. Consequently, SIDS has been correlated with infants sleeping facedown, in a prone position, though the cause of SIDS remains poorly understood and subject to controversy.

To prevent SIDS, many doctors advise that infants sleep on their backs. However, while a caretaker may place an infant on its back, it is nearly impossible to guarantee that the infant will not rollover in its sleep. Therefore, to alleviate the potential for danger, a caretaker may place barriers, such as pillows, alongside the infant to make rolling over more difficult. This simple method is not always effective and is usually coupled with a caretaker frequently checking the infant's sleeping position, either in person or with a video baby-monitor. However, a caretaker cannot watch an infant at all times and tragic accidents do still occur.

To further alleviate danger related to SIDS, systems have been developed which monitor the position of an infant. These systems include devices worn by the infant which continuously transmit position data to a base station. The base station may analyze the position data and detect when the infant has rolled into a facedown position. Unfortunately, such continuously transmitting systems may be cost prohibitive for widespread use, and may not adequately warn a caretaker of a dangerous situation when the transmitting device is unable to contact the base station.

Accordingly, what is needed is a method and system for reliably monitoring and determining when an infant is lying facedown and, consequently, alerting the infant's caretaker of the potentially dangerous situation.

SUMMARY OF THE INVENTION

Embodiments of the present invention generally relate to human monitoring devices and, more specifically, to detecting when an individual is lying in a predetermined position. In one embodiment, a method for detecting a predetermined position of a user wearing a disposable absorbent article may include detecting if the user of the disposable absorbent article is in the predetermined position, wherein the predetermined position is determined to be a potentially life-threatening position. The method may further include, in response to determining that the user is in the predetermined position, controlling an operation of a transmitter to perform one of: transmitting a signal and terminating the transmission of the signal, wherein at least the transmitter is located on the disposable absorbent article.

In another embodiment, a method for detecting a predetermined position of a user wearing a disposable absorbent article may include detecting, by a position detector, if the user of the disposable absorbent article is in the predetermined position, wherein the predetermined position is determined to be a potentially life-threatening position. The method may further include, in response to determining that the user is in the predetermined position, controlling an operation of a transmitter to perform one of: transmitting a signal and terminating the transmission of the signal, wherein at least the transmitter is located on the disposable absorbent article.

In yet another embodiment, a system for detecting a predetermined position of a user wearing a wearable item may include a position detector configured to detect if the user of the wearable item is in the predetermined position, wherein the predetermined position is determined to be a potentially life-threatening position. The system may further include a transmitter configured to respond when the user is in the predetermined position by performing one of: transmitting a signal and terminating the transmission of the signal, wherein at least the transmitter is located on the wearable item. In one embodiment, the wearable item is a disposable absorbent article, such as a diaper.

One embodiment provides a method for detecting a position of a user wearing a disposable absorbent article. The method includes providing a body position detection system operable according to whether the user is in a predetermined position predetermined to be a potentially life-threatening position, wherein at least one component of the body position detection system is located on the disposable absorbent article, and in response to the user assuming the predetermined position, controlling wireless communication with the at least one component by performing one of (i) allowing wireless communication with the at least one component, and (ii) preventing wireless communication with the at least one component. In a particular embodiment, the at least one component may provide a signal that conveys data from a position sensing device such as an inclinometer wherein the data can be interpreted to identify the position of the user. The signal may be read continuously, at regular or sporadic intervals, or in response to a request for data. In a particular embodiment, the at least one component may be a RFID device.

Another embodiment provides a method for detecting a predetermined position of a user wearing a wearable item. The method includes detecting, by a position detector of a body position detection system, that the user of the disposable absorbent article is in the predetermined position, wherein the predetermined position is determined to be a potentially life-threatening position, and in response to determining that the user is in the predetermined position, controlling wireless communication with an RFID tag of the body position detection system, wherein the RFID tag is located on the wearable item and wherein controlling wireless communication is performed by a controller located on the wearable item.

Another embodiment provides a system for detecting a predetermined position of a user wearing a wearable item. The system includes a position detector configured to detect whether the user of the wearable item is in the predetermined position, wherein the predetermined position is determined to be a potentially life-threatening position, and a transmitter located on the wearable item, wherein operation of the transmitter is controlled in response to the position detector detecting that the user is in the predetermined position by performing one of (i) establishing wireless communication with a receiving unit, and (ii) terminating wireless communication with the receiving unit. Additionally, or alternatively, the transmitter provides a signal that conveys data from the position detector.

Another embodiment provides a system for detecting a predetermined position of a user wearing a disposable absorbent article. The system includes a position detector and a RFID device located on the disposable absorbent article. The position detector is configured to detect whether the user of the disposable absorbent article is in the predetermined position, wherein the predetermined position is determined to be a potentially life-threatening position. The operation of the RFID device is controlled in response to the position detector detecting that the user is in the predetermined position by performing one of: (i) establishing wireless communication between the RFID device and a receiving unit, and (ii) terminating wireless communication between the RFID device and the receiving unit, or (iii) providing a signal that conveys data from a position sensing device. Additionally, or alternatively, the RFID device provides a signal that conveys data from the position detector.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention generally relate to human monitoring devices and, more specifically, to detecting when an individual is lying in a predetermined position. In various embodiments, at least one component of a monitoring system is disposed on a wearable item adapted to be worn by a person. In one embodiment, the wearable item is a disposable absorbent article, such as a diaper.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Furthermore, while the invention is described with reference to monitoring the position of an infant, it should be evident to one skilled in the art that the present invention may be used to monitor the position of a person of any age, or even an animal (e.g., dog, cat, and/or bear).

System for Monitoring the Position of an Infant

Figure 1:
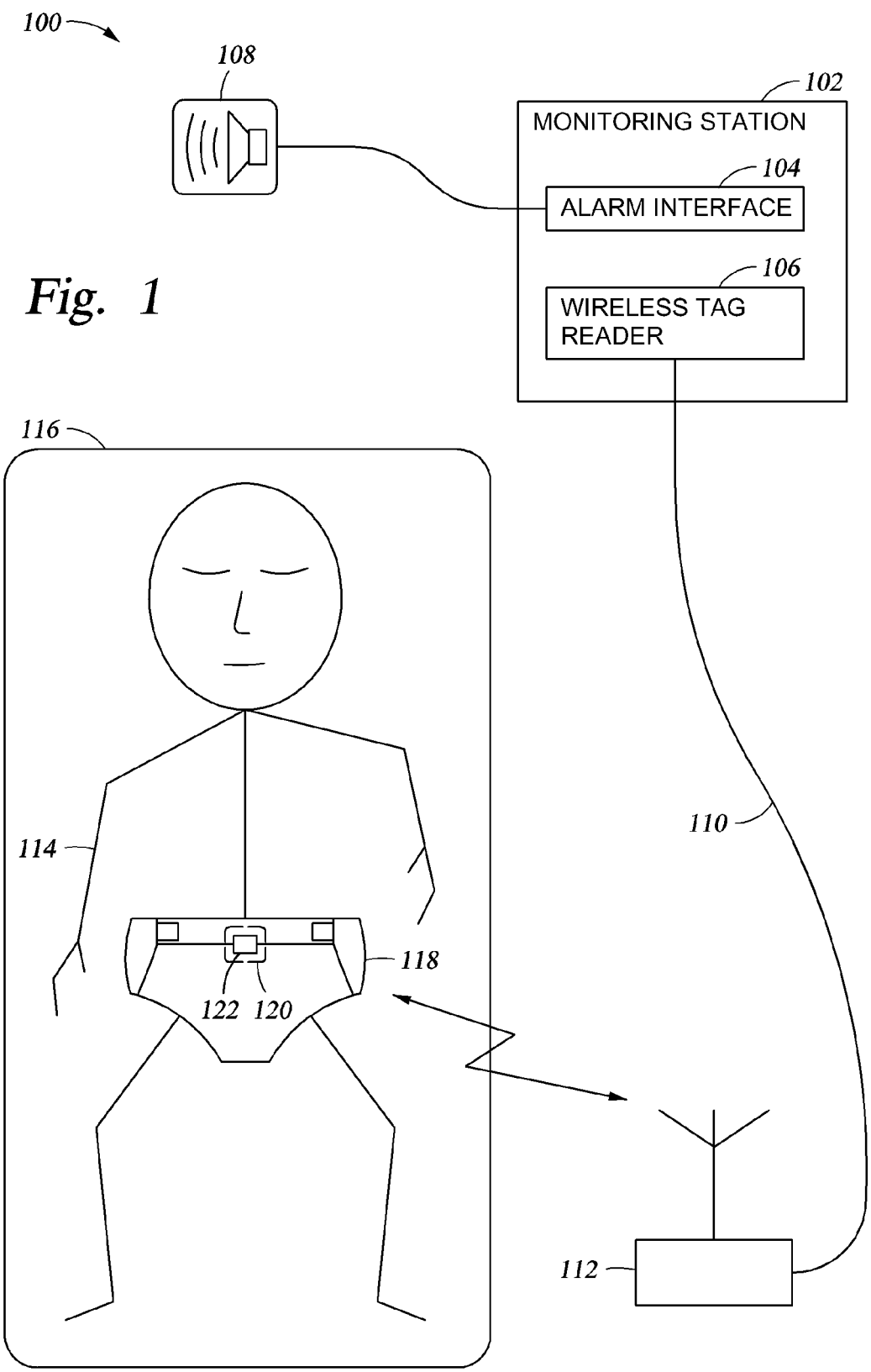
FIG. 1 illustrates a block diagram of a system for monitoring an infant's position, according to one embodiment of the invention.

FIG. 1 illustrates a block diagram of a system 100 for monitoring a position of an infant 114 (shown laying face-up on a surface, e.g., a mat 116), according to one embodiment of the invention. The system 100 may include an alarm device 108, a monitoring station 102, an absorbent article, e.g., a disposable diaper 118, worn by the infant 114, a position communicator 120 containing a wirelessly readable device 122, and at least one wireless reader antenna 112 connected to the monitoring station 102 by a cable 110.

The wirelessly readable device 122 may generally be any device configured to produce a signal capable of being detected by a receiving device. In a particular embodiment, the device 122 is an RFID tag and is, therefore alternatively referred to herein as the "tag 122". Accordingly, the tag 122 may include a transducer and an antenna, and may be encapsulated in a housing. It is contemplated that the RFID tag may be passive (in which case the tag is powered inductively by the signal received from a transmitting device) or active (in which case the tag is powered by an on-board battery). In the illustrative embodiment, the receiving device may include the antenna 112 and a wireless reader 106. The wireless reader 106 may include, for example, a transceiver and a decoder (to decode the signal received from the tag 122). In the event the device 122 is a RFID tag, the reader 106 is a RFID tag reader, and accordingly may alternatively be referred to herein as "the wireless tag reader 106". While, shown separately for illustration, it will be appreciated that the antenna 112 and the wireless tag reader 106 make up a RFID tag reader, according to one embodiment. However, while reference may be made to "tags" and "tag readers", such particular devices are merely illustrative and are not limiting of the invention.

In one embodiment, the monitoring station 102 may be provided as any variety of known systems capable of monitoring the infant 114, e.g., a computer, a baby monitor, a specialized microprocessor, and the like. The monitoring station 102 may be in a stand-alone product, or may be integrated into a product with multiple monitoring features. The invention, however, is not limited to any particular system and may be adapted to take advantage of new systems and devices as they become available.

In one embodiment, the monitoring station 102 may include the wireless tag reader 106 and an alarm interface 104. In addition to cooperating with the wireless tag reader antenna 112 to wirelessly read the wirelessly readable tag 122, the wireless tag reader 106 may also be configured to carry out other operations described herein, thereby enabling the monitoring station 102 to monitor the infant 114. For example, the reader 106 may interface with the alarm device 108 (via the alarm interface 104) to issue an alarm when appropriate.

The alarm interface 104 can be any appropriate interface depending on the type of alarm device 108. In one embodiment, the alarm device 108 may be a speaker, and an activated alarm device 108 may be indicated when the speaker emits a warning sound 402. Alternately, the alarm device may be another type of warning device, or may be an interface with a secondary infant monitor, such as a video monitor. The activated alarm may trigger activation of the secondary infant monitor. For example, the activated alarm may activate the video monitor so that a caregiver may view the infant's state from another location. In one embodiment, the alarm device 108 is a short range wireless device. For example, the alarm device 108 and the interface 104 may be a Bluetooth (or 802.11) device and interface, respectively. In another embodiment, the alarm device 108 located at a remote dispatch center and the interface 104 may be configured to issue a distress call. The distress call may result in an ambulance being dispatched to an address corresponding to where the distress call originated.

In one embodiment, one or more pressure sensors (not shown) in the mat 116 may control the operation of the wireless tag reader 106 such that the reader may only be operable when the one or more pressure sensors detect a pressure on the mat 116. In the absence of the requisite pressure, the reader 106 may be in a low power standby mode. This may reduce energy consumption by the monitoring station 102 and prolong the life of the components of the wireless tag reader 106.

The position communicator 120 may be configured to operate according to whether the infant 114 is in a predetermined position, such as a facedown position. It is also contemplated that the position communicator 120 may be configured to operate according more than one position.

In operation, the system 100 may wirelessly interrogate the wirelessly readable tag 122 and determine whether the tag 122 was read during the interrogation. Based on the results of the interrogation, the system 100 may identify whether or not the infant 114 lying on the mat 116 is in the predetermined position. In the case of SIDS prevention, the predetermined position may be when the infant 114 is lying facedown. However, more generally, the predetermined position may be any position (or even positions) for which notification is desired. If the system 100 detects that the infant is in one of the predetermined positions, an alarm may be issued to, e.g., a caregiver.

FIG. 1 is merely one configuration for the monitoring station 102. Embodiments of the present invention can apply to any comparable configuration, regardless of whether the monitoring station 102 is a multi-infant monitoring apparatus or a single-infant system.

A Sensor System for Predetermined Position Detection

Figure 2:
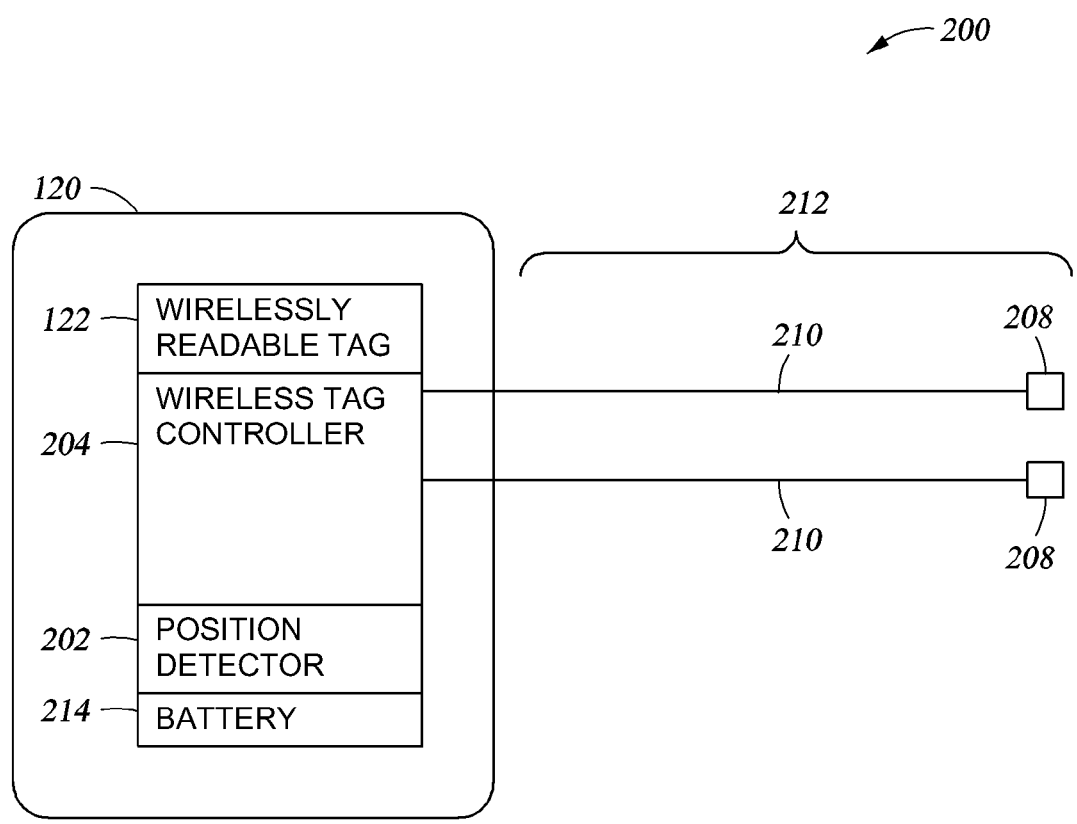
FIG. 2 illustrates a block diagram of a sensor system for detecting and indicating a predetermined position of the wearer of the sensor system, according to one embodiment of the invention.

FIG. 2 illustrates a block diagram of a wearable monitoring system 200 for detecting and indicating a predetermined position of the wearer of the wearable monitoring system 200, according to one embodiment of the invention. The system may include a position communicator 120 and a master power switch 212. In the illustrative embodiment, the position communicator 120 includes a position detector 202, a wireless tag controller 204, and a wirelessly readable tag 122.

In one embodiment, the position detector 202 may directly monitor the state of the infant 114 through at least one sensor. The sensor may be any type of sensor operable to determine the physical state of the infant 114. For example, the sensor may be a simple load sensitive switch and/or a complex micro-electromechanical system (MEMS) orientation sensor.

In one embodiment, if the sensor is a load sensitive switch, the switch may be placed on the infant's back-side so that when the switch is pressed (by virtue of the infant's weight), the infant 114 is not in the predetermined position. Alternatively, the load sensitive switch may be placed on the infant's front-side so that when the switch is pressed, the predetermined position is likely. In one embodiment, if the sensor is a MEMS orientation sensor, the output of the sensor may need to be interpreted in light of the sensor orientation (e.g., a positive voltage on the sensor may indicate that the sensor is pointing upwards and a negative voltage on the sensor may indicate that the sensor is pointing downwards). In one embodiment, the MEMS orientation sensor may be a 3-axis device in which a suspended weight induces readable voltage or resistance changes depending on orientation. In this way, the MEMS orientation sensor, in association with a transmitter (e.g., readable tag 122), could transmit the orientation state as a readable signal, or operate to turn the readable tag 122 on or off (i.e., selectively make the tag 122 readable by the reader 106). Exemplary MEMS orientation sensors are available from Microstrain, Inc. (Williston, Vt.).

In one embodiment, multiple sensors may be used in the position detector 202 or in addition to the position detector 202. The multiple sensors may each measure different parameters, including force, orientation, and position. The combination of these parameters and sensors may make the position detector 202 more accurate or provide different kinds of information. Exemplary devices may include motion detectors, sound detectors, pulse monitors, stress detectors, and the like. More particularly, MEMS accelerometer or inclinometer devices can be used, such as the inclinometer/accelerometer component families of VTI Technologies (Vantaa, Finland), and of Memsic Technologies (Andover, Mass.), and of Analog Devices, Inc. (Norwood, Mass.), and those described by A. Sadat et al. in "Low-power CMOS Wireless MEMS Motion Sensor for Physiological Activity Monitoring," in Regular Papers, IEEE Transactions on Circuits and Systems, December 2005, Volume 52, Issue 12, pages 2539-2551. Further examples of such devices include stress detectors that measure Galvanic skin response or other known factors, such as BodyMedia's SenseWear Armband (Pittsburgh, Pa.).

In one embodiment, the output of the position detector 202 may be interpreted by the wireless tag controller 204. Accordingly, the wireless tag controller may then permit or deny access to the wirelessly readable tag 122 by a wireless tag reader such as the wireless tag reader 106 and associated antenna 112. Depending on the configuration of the position detector 202 and the wireless tag controller 204, access to the wirelessly readable tag 122 may be enabled when the predetermined position is indicated by the position detector 202. Alternatively, access to the wirelessly readable tag 122 may be disabled when the predetermined position is indicated. Where multiple tags 122 are present, the tags 122 can be distinguished by their respective unique IDs. In other embodiments, position data (or other biometric information) may be continuously, periodically, or intermittently transmitted by the tag 122 and read by the reader 106. To this end, the tag 122 may include an encoder to encode the transmitted signal with the position (or other) data; the signal can then be decoded by the reader 106. In this way, output from any of the devices described above can be combined with wireless transmission circuitry (e.g., the transmitting device 122) to provide a wireless signal, such as an encoded RFID signal, that can be read with the reader 106 to provide information on position, body motion, orientation, body temperature, heart rate, etc.

In addition, the wearable monitoring system 200 may include output devices to stimulate the child. For example, the wearable monitoring system 200 may include an alarm device to provide an alarm signal such as a sound, a vibration, a cooling sensation, or other sensory signal to the child to awake the child if one or more sensors provides an indication of high risk (e.g., indication of decreased or stopped breathing). An example of a technology for providing vibration to awake an infant is the RespiSense Buzz device (South Africa).

Various methods of powering the system 200 are contemplated. In one embodiment, the wearable monitoring system 200 may obtain power through inductive coupling of the signal emitted by the wireless tag reader antenna 112. Alternatively, the predetermined position communicator 120 may be powered by a battery 214. The battery 214 may support processing by the wireless tag controller 204, power an active wirelessly readable tag 122, and/or power active sensors in the position detector 202. In one embodiment, the predetermined position communicator 120 may be configured to indicate when the battery is low. The predetermined position communicator 120 may have an audible alarm. Alternatively, the predetermined position communicator 120 may be configured to send a signal to the monitoring station 102 indicating the low battery, and the monitoring station 102 may trigger an alarm. So that battery-life of the battery 214 is not diminished while the predetermined position communicator 120 is not in use, a master power switch 212 may control access to the battery 214.

In one embodiment, the master power switch 212 may be a master arbiter of access to the predetermined position communicator 120. In this manner, the detection of the predetermined position may not be enabled unless the master power switch 212 is engaged. This may prevent false alarms from sensors that are not being used to monitor the infant 114, but are within range of the wireless tag reader antenna 112.

In one embodiment, the master power switch 212 may be connected to the wireless tag controller 204 by control lines 210. The switch 212 may prevent access to the battery 214 unless electrical contacts 208 are electrically connected. The contacts 208 may be included in a fastener, and may be electrically connected by closing the fastener. For example, the contacts 208 of the master power switch 212 may be electrically connected when closing snaps on a pair of pajamas, buttoning a pair of pants, or securing the tabs on a diaper, as will be discussed in more detail later. Alternatively, the contacts 208 may be electrically insulated from each other by a tab which, when removed, allows electrical contact between the contacts 208 and activates the wearable monitoring system 200.

In an alternative embodiment, access to the wirelessly readable tag 122 is not controlled by the wireless tag controller 204 and position detector 202. Instead, the wirelessly readable tag 122 and wireless tag reader 106 combination may be selected such that the wireless tag reader 106 is unable to read the wirelessly readable tag 122 through the body of the infant 114. In this manner, the body of the infant 114 may serve to block signal communication between the wirelessly readable tag 122 and the wireless tag reader 106. Therefore, the relative positions of the wireless tag reader antenna 112 and the wirelessly readable tag 122 will dictate whether the wirelessly readable tag 122 is readable by the wireless tag reader 106. In one embodiment, the wirelessly readable tag 122 is located on the front of the infant and the antenna 112 is located to the side or above the infant. In this configuration, communication between the tag 122 and the antenna 112 is possible so long as the infant is on its back (and possibly on its side). Once the infant turns over onto its stomach, however, communication between the tag 122 and the antenna 112 is blocked, in which case the system 100 issues an alarm via the alarm device 108. In an alternative embodiment, the tag 122 may be located on the infant's back, so that communication between the tag 122 and the antenna 112 is blocked so long as the infant remains on its back. Once the infant turns over onto its stomach, however, communication between the tag 122 and the antenna 112 is established, in which case the system 100 issues an alarm via the alarm device 108. It is contemplated that the system 100 allows user selection of where the position communicator 120 (and hence, the tag 122) will be placed. Accordingly, the system 100 may include a mode switch selectable by the user according to where the position communicator 120 is placed in a given case. In still another embodiment, the wireless tag reader antenna 112 may be embedded in the mat 116 the infant 114 lays on. In this case, communication between the tag 122 and the antenna 112 is possible so long as the tag 122 is proximate antenna 112, such as where the tag 122 is located on the infant's stomach and the infant is lying on its stomach. It is also contemplated that more than one antenna 112 may be provided to ensure desired communication.

In another embodiment, the wearable monitoring system 200 may include multiple wirelessly readable tags 122, each corresponding to one of a plurality of positions and each being uniquely identifiable (e.g., by virtue of a unique tag ID). In such a system, the position detector may be operable to differentiate between the plurality of positions, and the wireless tag controller 204 may select a wirelessly readable tag 122 corresponding to a specific position detected by the position detector 202. In this manner, the monitoring station 102 may have more resolution of the position of the infant 114 than in a wearable monitoring system 200 with a single wirelessly readable tag 122. Furthermore, since at least one wirelessly readable tag 122 may always be in communication with the wireless tag reader 106, this type of wearable monitoring system 200 may be used to monitor the presence of an infant 114. Such a wearable monitoring system 200 may be used as a tool to prevent kidnapping.

Garment for Infant Monitoring

Figure 3:
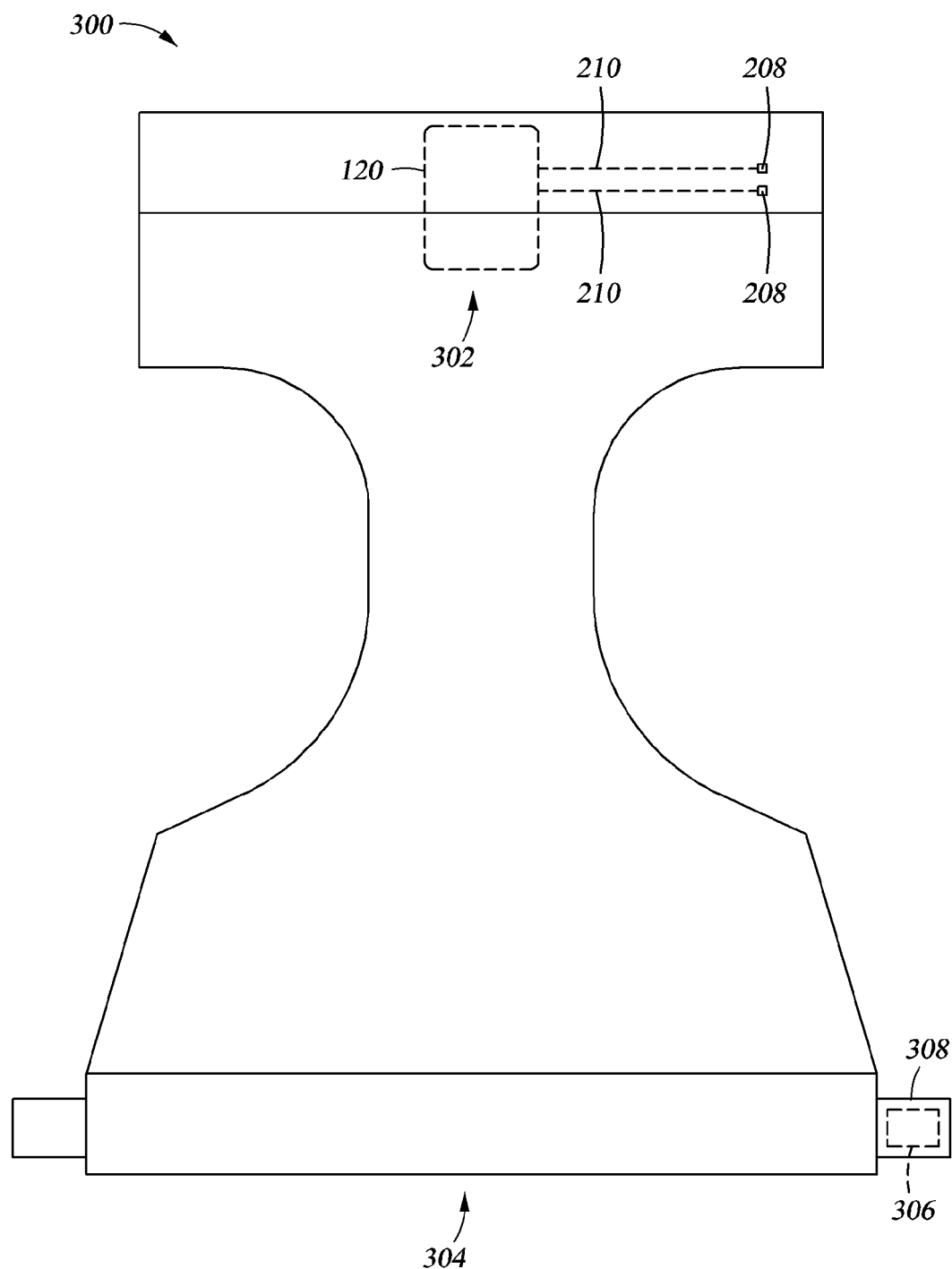
FIG. 3 illustrates a block diagram of a diaper to be worn by an infant whose position may be monitored, according to one embodiment of the invention.

FIG. 3 illustrates a block diagram of a disposable absorbent article, i.e., a diaper 300, to be worn by an infant 114 whose position may be monitored, according to one embodiment of the invention. The diaper 300 may be such that when worn by an infant, there is a front of the diaper 302 and a back of the diaper 304. The position communicator 120 may be attached to the diaper 300, and may be in the front of the diaper 302 or the back of the diaper 304.

In one embodiment, the predetermined position communicator 120, the control lines 210 and the contacts 208 may be at least partially disposed in the diaper 300. As depicted in FIG. 3, the contacts 208 may be located so that when the diaper is worn, a jumper 306 in a tab 308 of the diaper may electrically connect the contacts, thereby activating the position communicator 120 as described above.

In one embodiment, the position communicator 120 (and the rest of the wearable monitoring system 200) may be integrated into the diaper 300 during a manufacturing stage. For example, the position communicator 120 may be disposed between an outer and inner layer of material forming a portion of the diaper. The outer and inner layers may be portions of a conventional diaper or may be specifically provided for the purpose of housing the position communicator 120.

In another embodiment, the position communicator 120 may be a reusable device, while the control lines 210 and the contacts 208 may be permanently attached to the diaper 300. In this manner, the position communicator 120 may be a reusable unit that can be transferred from one diaper 300 to another without losing the functionality provided by the embedded control lines 210 and the contacts 208. It is contemplated that such a reusable position communicator 120 may be distributed and sold to consumers as a component of a unit of diapers or may be separately distributed and sold.

It is contemplated that the position communicator 120 may be enclosed in a moisture-resistant (e.g., polyurethane) housing to protect the circuitry from moisture and damage from impact. In the case of a position communicator 120 that is integrated into the diaper during manufacturing, the diaper materials themselves that enclose the communicator 120 may themselves provide this function.

In one embodiment, the wearable monitoring system 200 may be contained within a unit which may be attached to the diaper 300. The unit may be for a single use, or may be reusable and may be attached to the diaper 300 in a temporary manner. For example, the unit may be contained within a single-use sticker, so that any diaper 300 may be modified to allow for the monitoring of an infant 114 by simply placing the sticker on the diaper. Alternatively, the diaper 300 may include a pocket for inserting the unit, or Velcro® material to which the unit may be attached. In one embodiment, the unit may be large enough so that it does not present a choking hazard to the infant 114. It is also contemplated that removing the system 200 from the diaper (or other wearable item on which the system 200 is disposed) will disconnect a contact and cause the monitoring station 102 to issue an alarm via the alarm device 108.

One skilled in the art will recognize that while the invention is described above with respect to the diaper 300, the invention is not limited to this embodiment. For example, the wearable monitoring system 200 may be attached to any variety of wearable items including a pair or pants, a pair of underwear, a shirt, and/or pajamas. Further, the system may be secured to the wearable item by a button, a temporary fastener, tape, an adhesive, stitching, a Velcro® fastener, etc.

Exemplary Usage of the System for Monitoring the Position of an Infant

Figure 4:
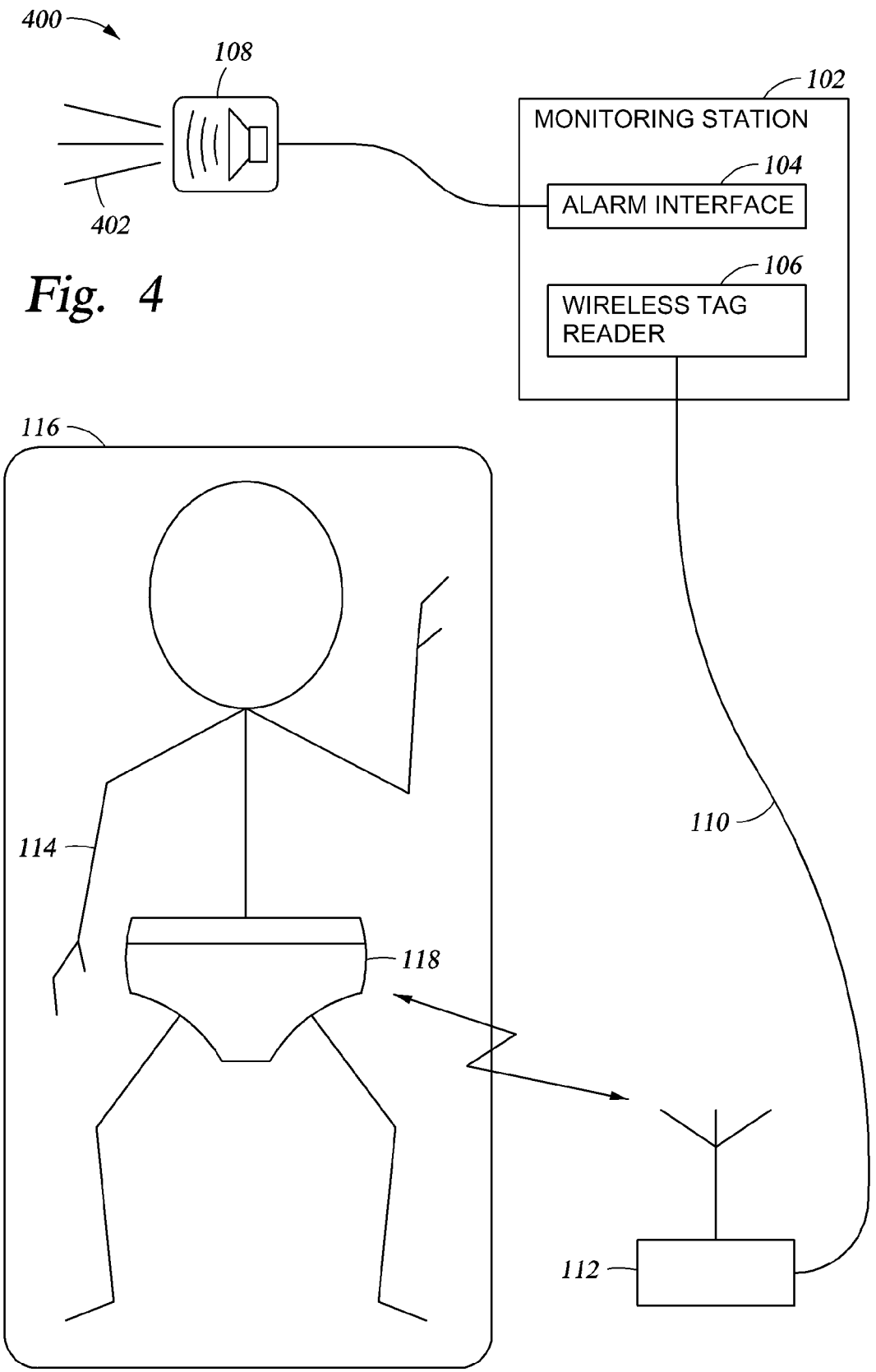
FIG. 4 illustrates a block diagram of the activated system for monitoring the infant's position when the infant is lying facedown, according to one embodiment of the invention.

FIG. 4 illustrates a block diagram of the activated system 400 for monitoring the infant's position when the infant 114 is lying facedown, according to one embodiment of the invention. In the depicted embodiment, the wearable monitoring system 200 may be enclosed in the front of the diaper 302, as is depicted in FIG. 1. Therefore, when the infant 114 rolls onto its stomach, the wearable monitoring system 200 may be between the infant and the mat 116.

Throughout the operation of the activated system 400, the tag reader 106 continuously, periodically or intermittently attempts to read the tag 122. However, the wireless tag controller 204 selectively allows communication between the tag 122 and the reader 106 depending on when the position detector 202 detects that the infant 114 is in a predetermined position. In one embodiment, the position detector 202 may detect that the infant 114 is lying facedown, and, in response, the wireless tag controller 204 may allow the wireless tag reader 106 access to the wirelessly readable tag 122. The monitoring station 102 may detect this access and may trigger the alarm interface 104 to activate an alarm device 108.

In another embodiment, a sensor in the position detector 202 may detect that the infant 114 is lying facedown, and, in response, the wireless tag controller 204 may terminate access by the wireless tag reader 106 to the wirelessly readable tag 122. The monitoring station 102 may detect this termination of access and may trigger the alarm interface 104 to activate the alarm device 108.

Process for Monitoring a Position of an Infant

Figure 5:
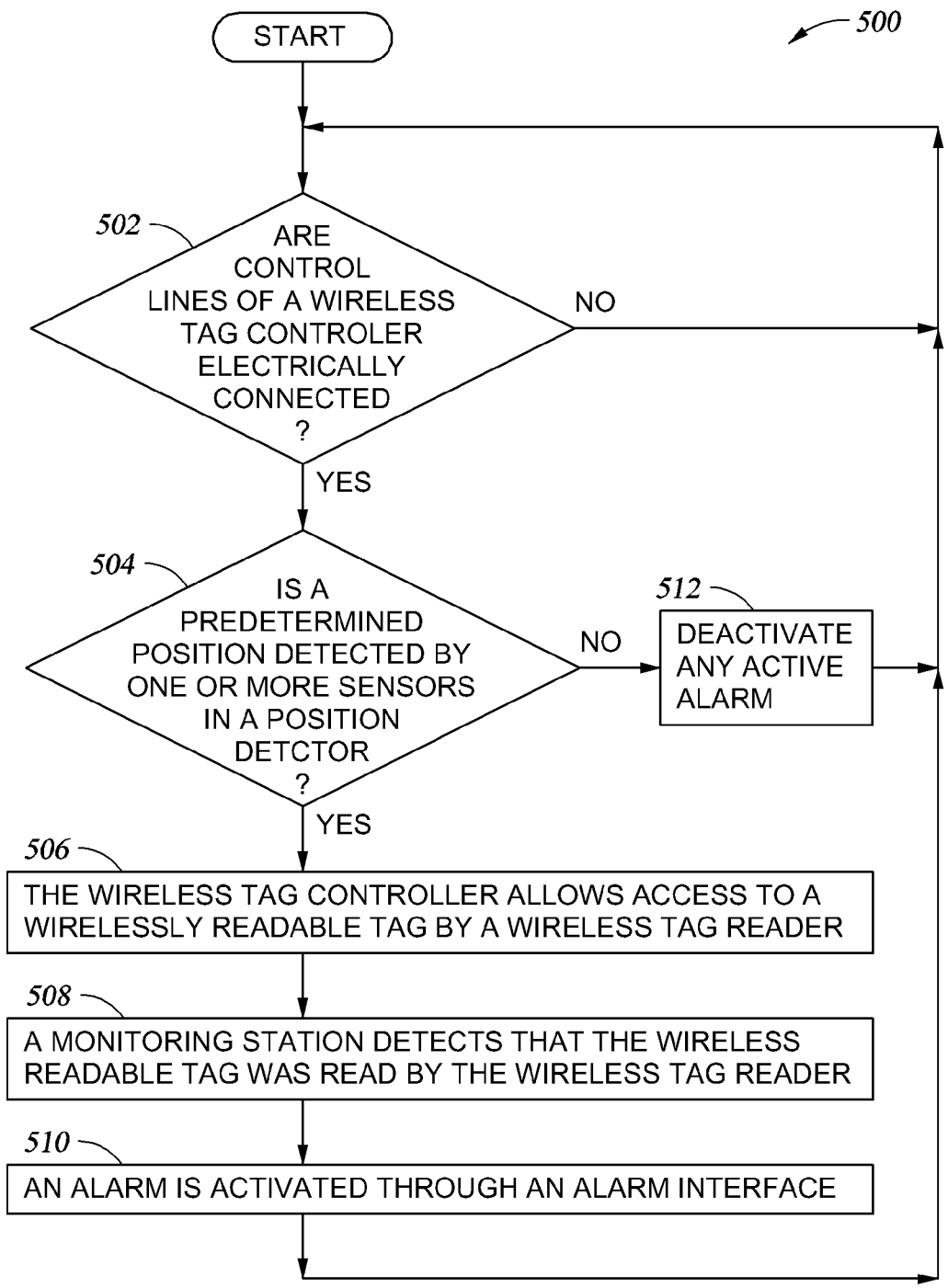
FIG. 5 illustrates a flow chart of the operation of the system for monitoring an infant, according to one embodiment of the invention.

FIG. 5 illustrates a flow chart of the operation 500 of the system for monitoring an infant 114, according to one embodiment of the invention. Although the process 500 may repeat in a loop, for illustrative purposes, the process 500 begins at step 502, where a determination is made as to whether control lines 210 of a wireless tag controller 204 are electrically connected, as described above. If the control lines 210 are not electrically connected, the process 500 may return to step 502.

Otherwise, in one embodiment, the process 500 may proceed to step 504, where a determination may be made as to whether a predetermined position was detected by one or more sensors in a position detector 202. In the case of SIDS prevention, the predetermined position may be when the infant 114 is lying facedown.

In one embodiment, if the predetermined position is not detected, the process 500 may proceed to step 512, where any activated alarms in the monitoring station 102 may be deactivated. The process 500 may then return to step 502.

Otherwise, in one embodiment, the predetermined position is detected, and the process 500 may proceed to step 506. In step 506, the wireless tag controller 204 may allow access to the wirelessly readable tag 122 by a wireless tag reader 106 which the wireless tag reader 106 could not access when the infant 114 was not in the predetermined position.

In step 508, a monitoring station 102 may determine that the wirelessly readable tag 122 was read by the wireless tag reader 106. If such a determination is made, the process 500 may proceed to step 510, where an alarm is issued (e.g., via the device 108 through the alarm interface 104).

As described above, the process 500 may repeat in a loop. Accordingly, the process 500 may return to step 502. The process may repeat until the monitoring station 102 is deactivated.

In one alternate embodiment, the detection of the predetermined position may cause the wireless tag controller 204 to terminate access to the wirelessly readable tag 122. In this case, the wireless tag reader 106 may no longer be able to access the wirelessly readable tag 122. The monitoring station 102 may detect that the wirelessly readable tag 122 is no longer accessible, and may activate the alarm 108 through the alarm interface 104.

In one embodiment, the wireless tag controller 204 may wait for a predetermined period of time upon detection of the predetermined position before activating the alarm 108. The monitoring station 102 may delay activating the alarm 108 in order to give the infant 114 an opportunity to move out of the predetermined position. Delaying activation of the alarm 108 may reduce false-alarms that may unnecessarily burden a caretaker. Furthermore, the same result may be achieved if the position detector 202 waits for a predetermined period of time before indicating the prone position. Alternatively, the predetermined period of time may be zero-seconds, and activation of the alarm 108 may not be delayed.

In one embodiment, the wireless tag controller 204 may wait for a predetermined period of time upon detection that the infant 114 is no longer in the predetermined position before deactivating the alarm 108. Delaying deactivation of the alarm 108 may prevent deactivating the alarm, while a potentially dangerous situation persists. Furthermore, the same result may be achieved if the position detector 202 waits for a predetermined period of time before indicating the infant 114 is not in prone position. Alternatively, the predetermined period of time may be zero-seconds, and deactivation of the alarm 108 may not be delayed.

In the foregoing embodiments are provided for monitoring the position of a person. However, it is contemplated that the movement of the person may also be detected and monitored using the apparatus and methods described herein. For example, the position data accumulated over a period of time for a give person, may collectively describe the movement of the person. Further, the location of a person may be monitored using the apparatus and methods described herein. For example, the system 100 may include RFID tags on opposite sides of a diaper or garment—one tag that is active when the person is face-up and another that is active when the person is facedown (e.g., the tags may be activated by the provision of respective pressure-switches that connect the RFID chip and its respective antenna when sufficient pressure is applied to the respective pressure-switch). In this way, one RFID tag always active whether the person is face-up or facedown and the position of the person can therefore be monitored in this way (on this basis of which unique ID is being read). However, the inactivity of both RFID tags may indicate that the person has been removed from the monitored location (i.e., the RFID tags are too remote to be read). Accordingly, an alarm may be issued. The foregoing embodiment may be particularly advantageous as a kidnapping preventative, although persons skilled in the art will recognize other applications within the scope of the invention.

Further, embodiments of the present invention facilitate monitoring multiple persons in a common environment. For example, it may be desirable to monitor a plurality of infants in a nursery. The provision of RFID tags associated with each infant allows the infants to be distinguished from one another. That is, since each RFID tag has a unique ID, a RFID tag reader positioned to read each of the plurality of tags can distinguish between the tags and, hence, between the infants.

CONCLUSION

Advantageously, embodiments of the invention allow the monitoring of a position of an infant or other user. In a particular embodiment, detection of the infant lying facedown is permitted, where the infant may be susceptible to apnea and asphyxiation, possibly resulting in the death of the infant from Sudden Infant Death Syndrome.

While the foregoing is directed to embodiments of the present invention, other and further embodiments of the invention may be devised without departing from the basic scope thereof, and the scope thereof is determined by the claims that follow.

What is claimed is:

1. A method for detecting a position of a user wearing a disposable absorbent article, the disposable absorbent article comprising a first electrical contact, a second electrical contact, and a tab electrically insulating the first electrical contact from the second electrical contact, wherein removal of the tab enables activation of a body position detection system by enabling a connection between the first electrical contact and the second electrical contact when the disposable absorbent article is worn by the user, the method comprising:
   providing the body position detection system operable according to whether the user is in a predetermined position predetermined to be a potentially life-threatening position and whether the first electrical contact is electrically connected to the second electrical contact, wherein removal of the tab activates the position detector by enabling the first electrical contact to be connected to the second electrical contact wherein at least one component of the body position detection system includes transmitting circuitry and is located on the disposable absorbent article; and
   in response to the user assuming the predetermined position, controlling wireless communication with the at least one component, by performing one of:
   (i) allowing wireless communication with the at least one component; and
   (ii) preventing wireless communication with the at least one component; wherein the predetermined position corresponds to a heightened risk for Sudden Infant Death Syndrome.

2. The method of claim 1, wherein the at least one component is a wirelessly readable tag.

3. The method of claim 1, further comprising, responsive to the controlling wireless communication with the at least one component, indicating by a monitoring station that the predetermined position of the user is detected; wherein indicating by the monitoring station occurs only if the user is in the predetermined position longer than a predetermined period of time.

4. The method of claim 1, wherein the disposable absorbent article is a diaper (SIDS).

5. The method of claim 1, wherein the at least one component is at least partially disposed between an outer layer and an inner layer of the disposable absorbent article.

6. The method of claim 1, wherein the at least one component is an RFID device and wherein the body position detection system further includes a controller located on the disposable absorbent article and configured to control the wireless communication with the REID device.

7. The method of claim 1, further comprising, detecting that the user has assumed the predetermined position; wherein the detecting is performed by one or more sensors of the body position detection system, the one or more sensors operable to detect one or more of force and orientation according to whether the user is in the predetermined position.

8. A method for detecting, by a position detector of a body position detection system, a predetermined position of a user wearing a wearable item, the wearable item comprising a first control line and a second control line coupled to the position detector and at least partially disposed in the wearable item, a first electrical contact coupled to the first control line, a second electrical contact coupled to the second control line, and a tab insulating the first and second control lines such that a removal of the tab enables an electrical contact between the first and the second contacts via a jumper positioned to electrically connect the first electrical contact to the second electrical contact when the wearable item is worn by the user, the position detector being active only when the first electrical contact is connected to the second electrical contact, the method comprising:
   activating the position detector, wherein removal of the tab activates the position detector;
   detecting, by the position detector, that the user of the disposable absorbent article is in the predetermined position, wherein the predetermined position is determined to be a potentially life threatening position; and
   in response to determining that the user is in the predetermined position, controlling wireless communication with an REID device of the body position detection system; wherein the REID device is located on the wearable item; and wherein controlling wireless communication is performed by a controller located on the wearable item; wherein the predetermined position corresponds to a heightened risk for Sudden Infant Death Syndrome.

9. The method of claim 8, wherein controlling wireless communication comprises allowing wireless communication with the REID device by a REID device reader.

10. The method of claim 8, further comprising, responsive to the controlling wireless communication with the REID device, indicating by a monitoring station that the predetermined position of the user is detected; wherein indicating by the monitoring station occurs only if the user is in the predetermined position longer than a predetermined period of time.

11. The method of claim 8, wherein the wearable item is a diaper.

12. The method of claim 8, wherein the wearable item is a disposable absorbent article and wherein the position detector and the REID device are at least partially disposed between layers and of the disposable absorbent article.

13. The method of claim 8, wherein the position detector consists of one or more pressure switches communicatively coupled to the controller in a manner operable to control the wireless communication with the REID device.

14. A system for detecting a predetermined position of a user wearing a wearable item, the system comprising:
a first electrical contact and a second electrical contact coupled to the wearable item;
a tab electrically insulating the first electrical contact from the second electrical contact;
a connector positioned to electrically connect the first electrical contact to the second electrical contact when the wearable item is worn and the tab is removed;
a position detector configured to detect that the user of the wearable item is in the predetermined position, the position detector being active only when the first electrical contact is connected to the second electrical contact, wherein the predetermined position is determined to be a potentially life-threatening position; and
a transmitter located on the wearable item, wherein operation of the transmitter is controlled in response to the position detector detecting that the user is in the predetermined position by performing one of:
(i) establishing wireless communication with a receiving unit; and
(ii) terminating wireless communication with the receiving unit; wherein the detection of the predetermined position indicates to a heightened risk for Sudden Infant Death Syndrome.

15. The system of claim 14, further comprising a monitoring station configured to indicate detection of the predetermined position of the user according to the state of wireless communication between the receiving unit and the transmitter; wherein the monitoring station indicates the predetermined position only if the user remains in the predetermined position longer than a predetermined period of time.

16. The system of claim 14, wherein the position detector and the transmitter are attached to the wearable item.

17. The system of claim 14, wherein the position detector consists of one or more pressure switches communicatively coupled to the transmitter in a manner operable to control the wireless communication between the transmitter and the receiving unit.

18. The system of claim 14, wherein the position detector consists of one or more sensors operable to detect one or more of force, orientation, a physical property, and position.

19. A system for detecting a predetermined position of a user wearing a disposable absorbent article, the system comprising:
a first electrical contact and a second electrical contact coupled to the disposable absorbent article;
a tab electrically insulating the first electrical contact from the second electrical contact;
a connector positioned to electrically connect the first electrical contact to the second electrical contact when the disposable absorbent article is worn and the tab is removed;
a position detector configured to detect that the user of the disposable absorbent article is in the predetermined position, the position detector being active only when the first electrical contact is connected to the second electrical contact, wherein the predetermined position is determined to be a potentially life threatening position; and
an REID tag located on the disposable absorbent article, wherein operation of the REID tag is controlled in response to the position detector detecting that the user is in the predetermined position by performing one of:
(i) establishing wireless communication between the REID tag and a receiving unit; and
(ii) terminating wireless communication between the REID tag and the receiving unit; wherein the predetermined position corresponds to a heightened risk for Sudden Infant Death Syndrome.

20. The system of claim 19, wherein the disposable absorbent article is a diaper and the REID tag is at least partially disposed between an outer layer and an inner layer of the diaper.

21. The system of claim 19, wherein the REID tag is releasably attached to the disposable absorbent article in a manner allowing removal of the REID tag from the disposable article and subsequent reuse of the REID tag.

22. The system of claim 14, further comprising a battery, wherein the position detector is powered by the battery when the first electrical contact is electrically connected to the second electrical contact.

* * * * *

UNITED STATES PATENT AND TRADEMARK OFFICE
CERTIFICATE OF CORRECTION

PATENT NO. : 7,733,233 B2
APPLICATION NO. : 11/552481
DATED : June 8, 2010
INVENTOR(S) : O'Shea et al.

It is certified that error appears in the above-identified patent and that said Letters Patent is hereby corrected as shown below:

In claim 1, column 12, line 16, after "Death Syndrome" insert --(SIDS)--;

In claim 4, column 12, line 27, after "article is a diaper" delete "(SIDS)";

In claim 6, column 12, line 35, delete "REID" and insert --RFID--;

In claim 8, column 12, line 66, delete "REID" and insert --RFID--;

In claim 8, column 12, line 67, delete "REID" and insert --RFID--;

In claim 9, column 13, line 8, after "with the" delete "REID" and insert --RFID--, and after "device by a" delete "REID" and insert --RFID--;

In claim 10, column 13, line 10, delete "REID" and insert --RFID--;

In claim 12, column 13, line 19, delete "REID" and insert --RFID--;

In claim 13, column 13, line 24, delete "REID" and insert --RFID--;

In claim 19, column 14, line 31, delete "REID" and insert --RFID--;

In claim 19, column 14, line 32, delete "REID" and insert --RFID--;

In claim 19, column 14, line 36, delete "REID" and insert --RFID--;

In claim 19, column 14, line 38, delete "REID" and insert --RFID--;

Signed and Sealed this

Twenty-sixth Day of October, 2010

David J. Kappos
*Director of the United States Patent and Trademark Office*

In claim 20, column 14, line 42, delete "REID" and insert --RFID--;

In claim 21, column 14, line 45, delete "REID" and insert --RFID--;

In claim 21, column 14, line 47, delete "REID" and insert --RFID--;

In claim 21, column 14, line 48, delete "REID" and insert --RFID--.